United States Patent [19]

Swartz et al.

[11] Patent Number: 5,715,818
[45] Date of Patent: Feb. 10, 1998

[54] METHOD OF USING A GUIDING INTRODUCER FOR LEFT ATRIUM

[75] Inventors: John Frederick Swartz, Tulsa, Okla.; John D. Ockuly; John J. Fleischhacker, both of Minnetonka, Minn.; James A. Hassett, Bloomington, Minn.

[73] Assignee: Daig Corporation, Minnetonka, Minn.

[21] Appl. No.: 551,173

[22] Filed: Oct. 31, 1995

Related U.S. Application Data

[62] Division of Ser. No. 147,168, Nov. 3, 1993, Pat. No. 5,497,774.

[51] Int. Cl.⁶ .................................................. A61B 5/00
[52] U.S. Cl. .................. 128/642; 128/772; 128/658; 128/657; 604/280; 604/282; 607/122
[58] Field of Search ............................ 128/642, 656, 128/657, 658, 662.06, 772; 604/280, 282; 607/122; 606/41

[56] References Cited

U.S. PATENT DOCUMENTS

| | | | |
|---|---|---|---|
| 4,922,910 | 5/1990 | Kanai et al. | 128/642 |
| 5,427,119 | 6/1995 | Swartz et al. | 128/657 |
| 5,476,495 | 12/1995 | Kordis et al. | 128/642 |
| 5,549,581 | 8/1996 | Lurie et al. | 128/642 |

FOREIGN PATENT DOCUMENTS 0241688  12/1986  German Dem. Rep. ............ 128/642

*Primary Examiner*—Jennifer Bahr
*Assistant Examiner*—Stephen Huane
*Attorney, Agent, or Firm*—Scott R. Cox

[57] ABSTRACT

A guiding introducer for use in the left atrium comprised of a first, second and third section wherein the first section is a generally elongated straight section wherein merged with the distal end of the first section is a second section which is curved in a compound curve, first curving upward in a first longitudinal curve and simultaneously curving to the right in a second longitudinal curve, wherein the second section merges with the third section wherein said third section is a third longitudinal curve wherein the plane of the third section is angled upward at an angle of approximately 25 to about 60 degrees from the plane of the first section and wherein substantially all of the third section is coplanar.

13 Claims, 6 Drawing Sheets

SHEATH & CATHETER
IN
RIGHT ATRIUM

1. TRICUSPID VALVE
2. SHEATH
3. CATHETER

SHEATH & CATHETER IN RIGHT ATRIUM

1. TRICUSPID VALVE
2. SHEATH
3. CATHETER

SHEATH & CATHETER IN LEFT ATRIUM

1. CORONARY SINUS
2. MITRAL VALVE
3. FOSSA OVALIS (PATENT)
4. SHEATH
5. CATHETER

METHOD OF USING A GUIDING INTRODUCER FOR LEFT ATRIUM

This is a divisional of application Ser. No. 08/147,168 filed on Nov. 3, 1993, now U.S. Pat. No. 5,497,774.

BACKGROUND OF THE INVENTION

1. Field of Invention

This invention relates to introducers. More particularly, this invention relates to guiding introducers of specific shapes for use within the left atrium of the human heart.

2. Prior Art

Introducers and catheters have been in use for medical procedures for many years. For example, one use has been to convey an electrical stimulus to a selected location within the human body. Another use is to monitor and make measurements for diagnostic tests within the human body. Thus, catheters may examine, diagnose and treat while positioned at a specific location within the body which are otherwise inaccessible without more invasive procedures. In use, catheters may be inserted into a major vein or artery which is near the body surface. These catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such preciseplacement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflict with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 4,117,836 discloses a catheter for the selective coronary angiography of the left coronary artery and U.S. Pat. Nos. 5,016,640 and 4,883,058 disclose catheters for selective coronary angiography of the right coronary artery. See also U.S. Pat. No. 4,033,031. Finally, U.S. Pat. No. 4,898,591 discusses a catheter with inner and outer layers containing braided portions. The '591 patent also discloses a number of different curvatures for intravascular catheters.

Thus, there are a number of patents which disclose catheters with predetermined shapes, designed for use in specific medical procedures generally associated with the heart or the vascular system. Because of precise physiology of the heart and the vascular system, catheters or introducers with carefully designed shapes for predetermined uses within the human heart and vascular system are important.

Accordingly, it is an object of this invention to prepare a guiding introducer for selected medical procedures in the left atrium.

It is a further object of this invention to prepare a guiding introducer for use in selected electrophysiology procedures within the left atrium of the heart.

Another object of this invention is to prepare a guiding introducer for use in selected ablation procedures within the left atrium of the heart.

These and other objects are obtained by the design of the guiding introducers disclosed in the instant invention.

SUMMARY OF INVENTION

The instant invention is a guiding introducer to be used in the left atrium comprised of a first, second and third sections wherein the first section is a generally elongated straight section which is merged at its distal end with the second and third sections which form a complex curve.

DETAILED DESCRIPTION OF THE DRAWINGS

Figure 1:
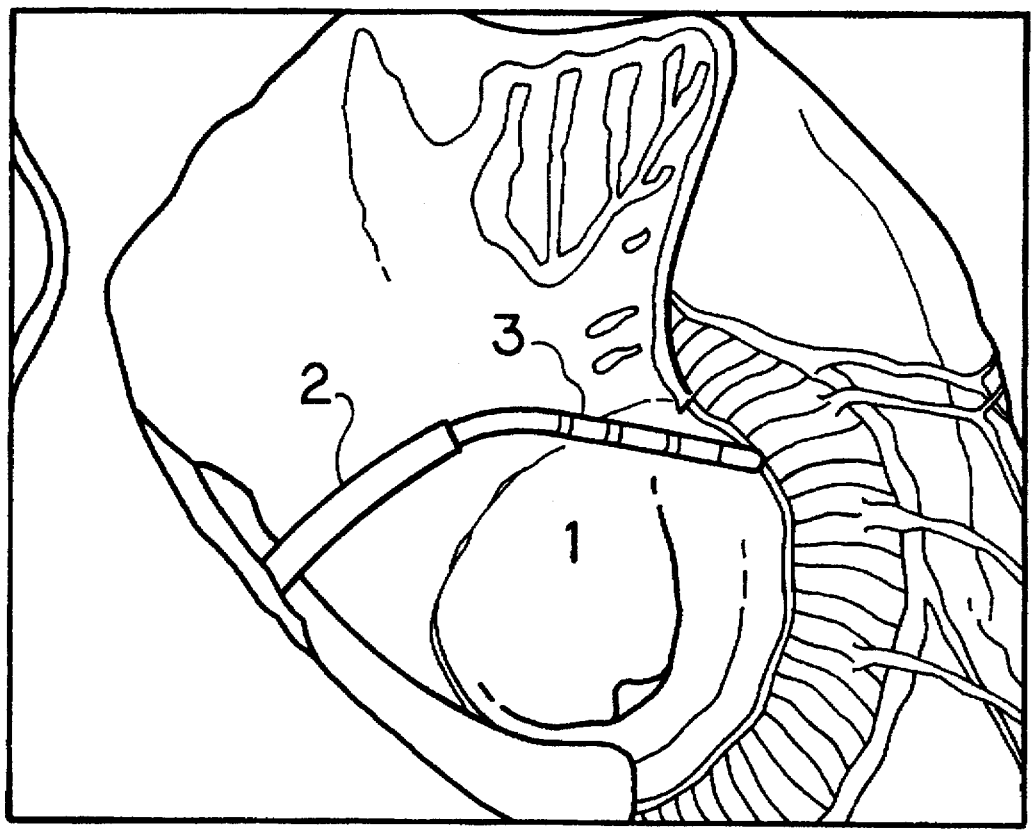
FIG. 1 is a cross-section of the right side of the heart showing the right atrium and ventricle and the placement of the guiding introducer.
Figure 2:
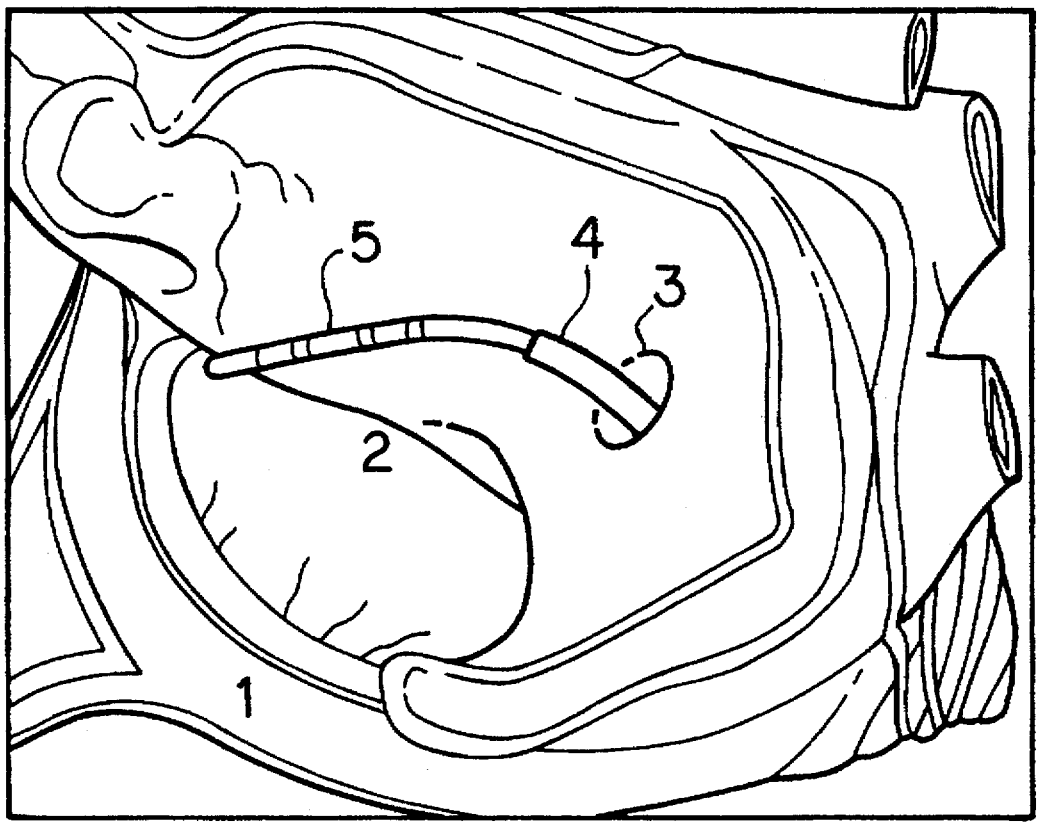
FIG. 2 is a cross-section of the left side of the heart showing the mitral valve and the placement of the guiding introducer.
Figure 3:
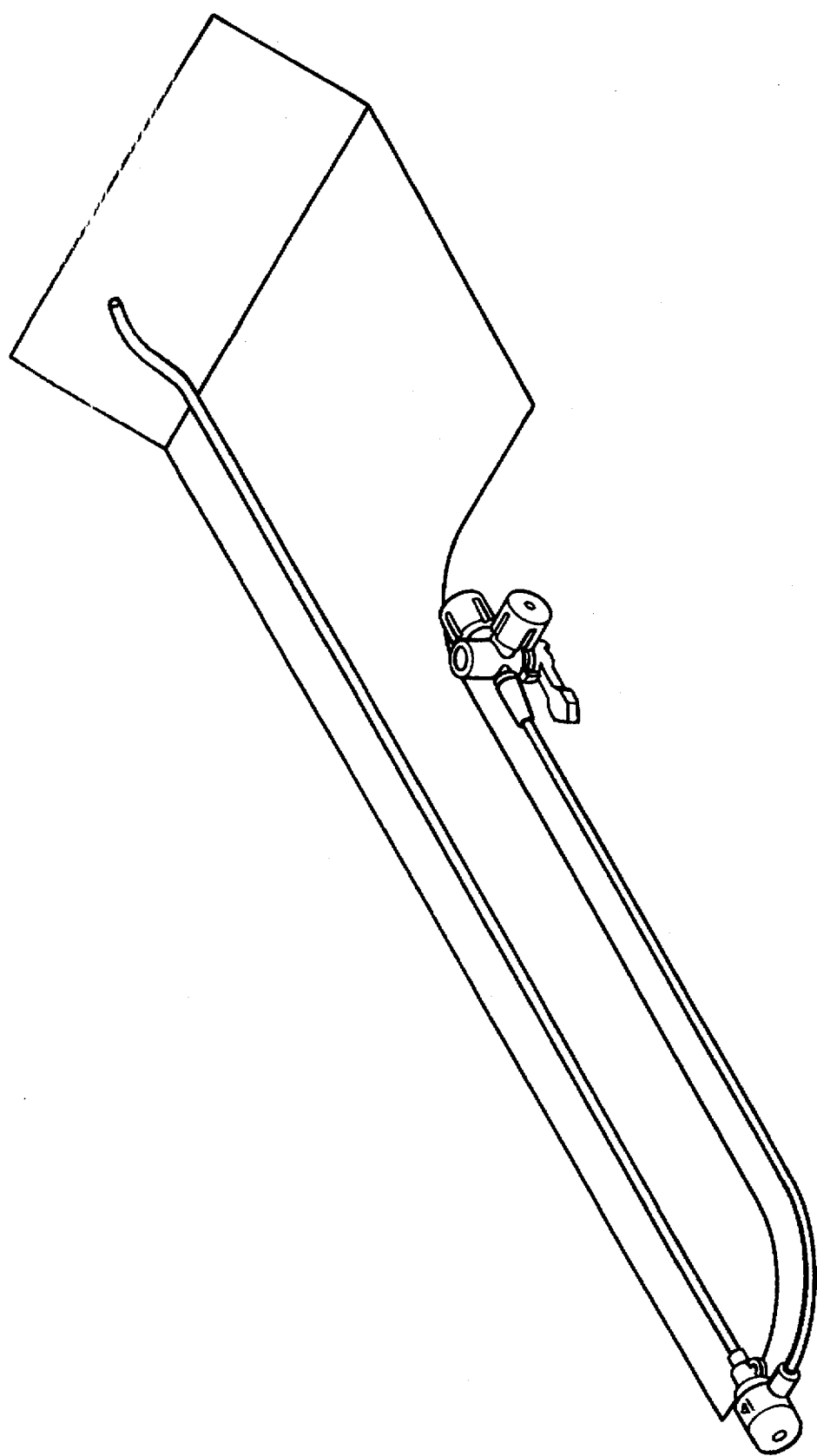
FIG. 3 is a perspective view of one embodiment of the guiding introducer.
Figure 4:
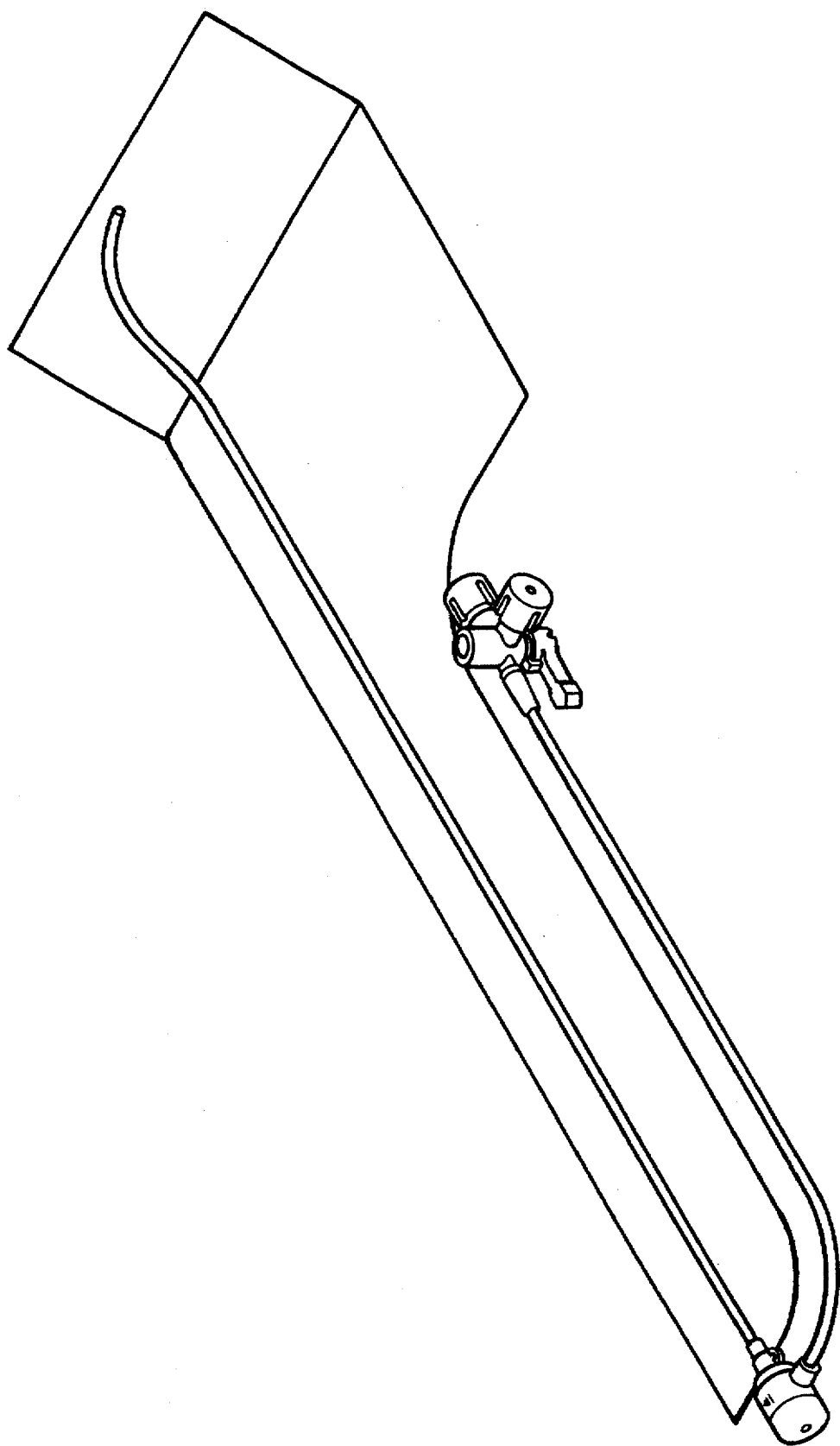
FIG. 4 is a perspective view of a second embodiment of the guiding introducer.
Figure 5:
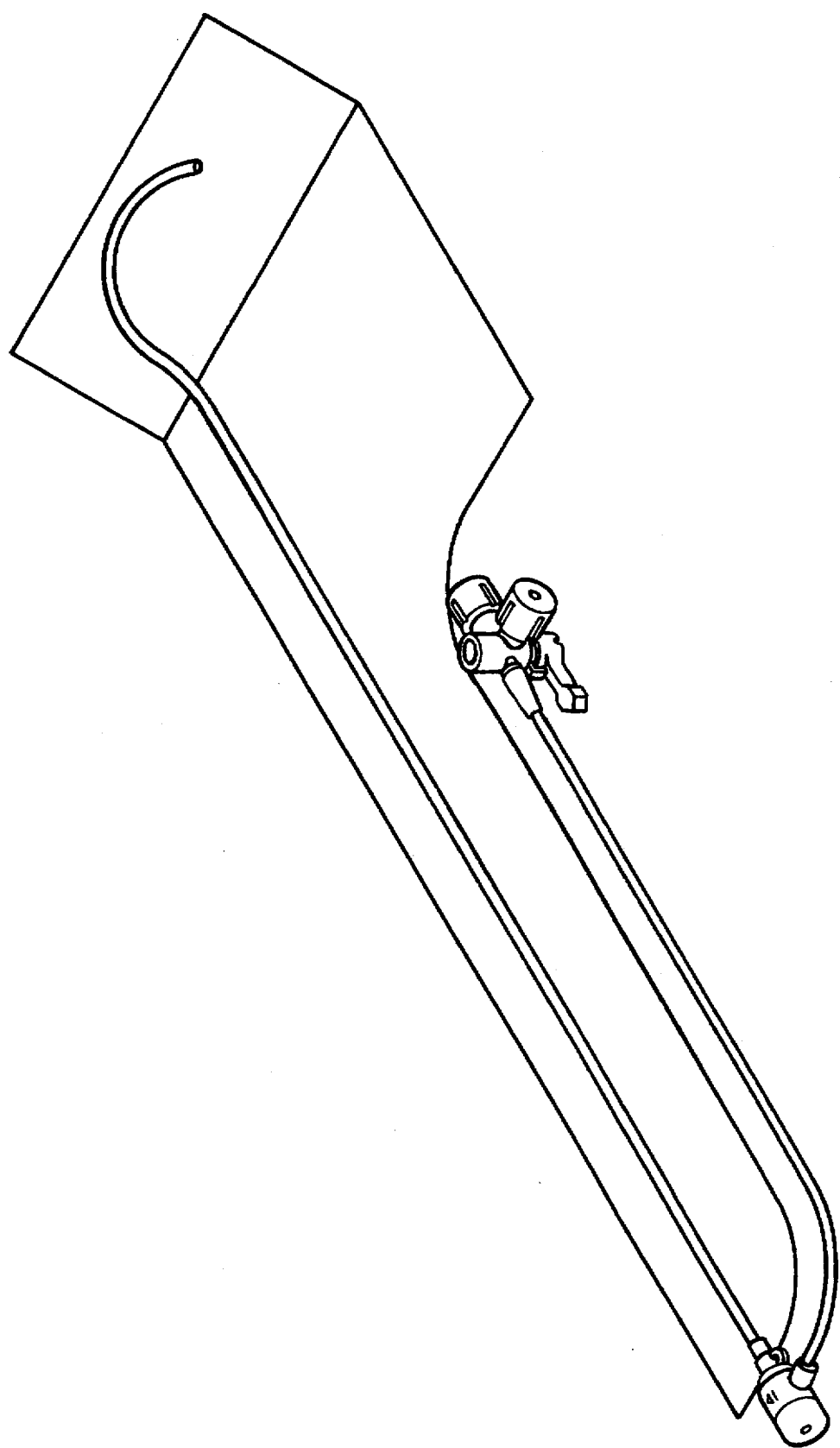
FIG. 5 is a perspective view of a third embodiment of the guiding introducer.
Figure 6:
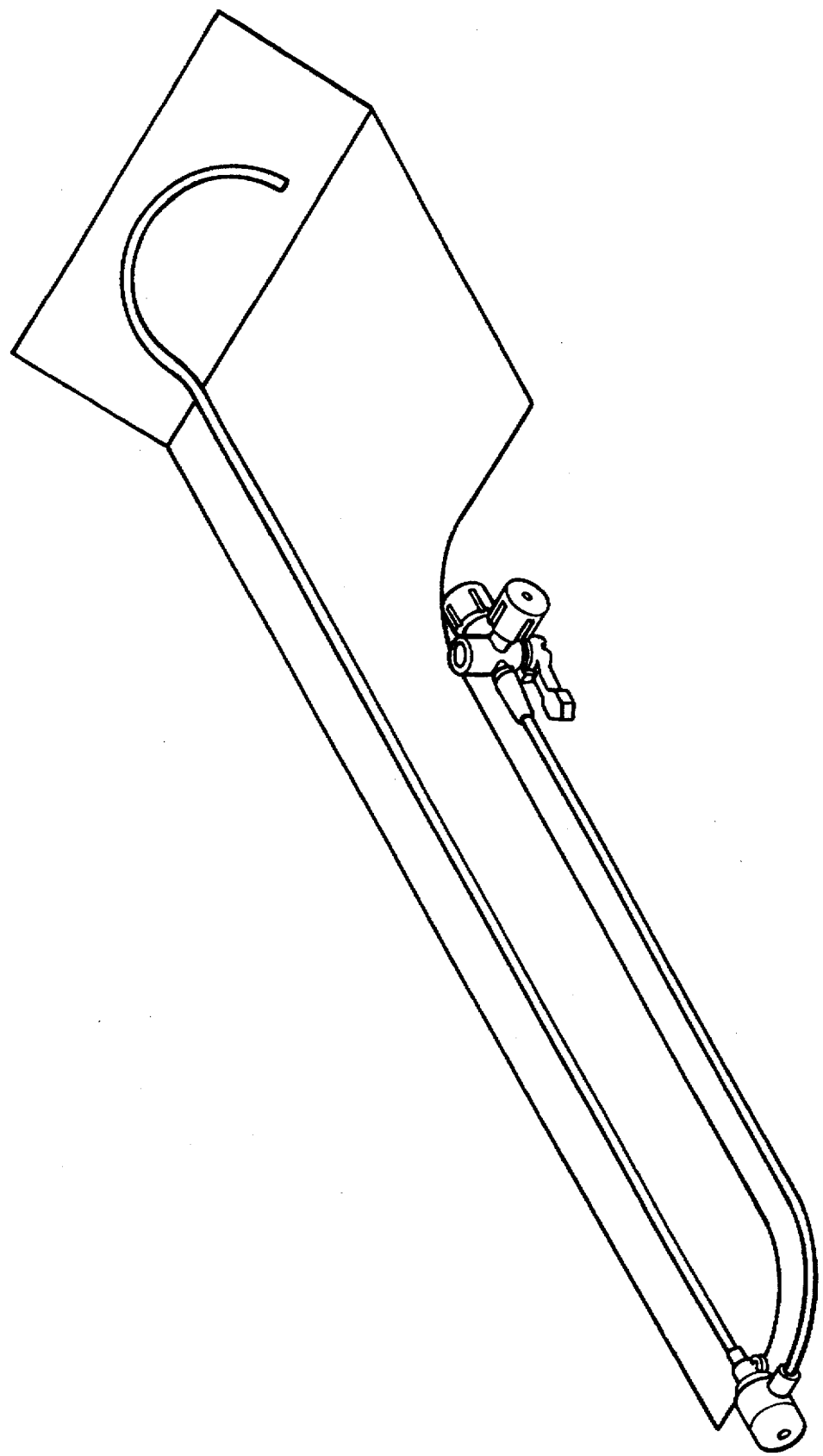
FIG. 6 is a perspective view of a fourth embodiment of the guiding introducer.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a recessed portion, the fossa ovalis. See FIGS. 1 and 2. In the heart of a fetus, the fossa ovalis is open, permitting the fetal blood to flow between the right and left atria. In most individuals, this opening closes after birth, but in as many as 25 percent of individuals an opening still remains in the fossa ovalis between the right and left atria. Between the fossa ovalis and the tricuspid valve is the opening or ostium for the coronary sinus. The coronary sinus is the large epicardial vein which accommodates most of the venous blood which drains from the myocardium into the right atrium.

In the normal heart, contraction and relaxation of the heart muscle (myocardium) takes place in an organized fashion as electro-chemical signals pass sequentially through the myocardium from the atrial to the ventricular tissue along a well defined route which includes the His-Purkinje system. Initial electric impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, a common arrhythmia is Wolff-Parkinson-White syndrome (W-P-W). The cause of W-P-W is the existence of an anomalous conduction pathway or pathways that connects the atria muscle tissue directly to the ventricular muscle tissue, thus by-passing the normal His-Purkinje system. These pathways are usually located in the fibrous tissue that connect the atrium and the ventricle. In recent years a technique has been developed to destroy these anomalous conduction pathways by delivering energy into the tissue in which the pathways exist. To accomplish this procedure a special electrode catheter is positioned as close as possible to the anomalous conduction pathway to maintain constant tissue contact while energy is delivered to destroy the pathway. This same type of contact with the cardiac tissue is also necessary when mapping or other procedures are employed relating to these pathways.

One end of these anomalous conduction pathways can be located either in the right atrium or in the left atrium with the other end of the pathway located in the ventricle. When the anomalous conduction pathway is located between the left atrium and the left ventricle, there are two approaches to positioning the catheter near that pathway for the appropriate medical procedure. One is to introduce the catheter into the femoral artery by a standard introducer sheath and advance it up the aorta, across the aortic valve into the left ventricle and then attempt to position its tip under the mitral valve annulus near the anomalous conduction pathway. This approach is frequently difficult for many reasons, including the difficulty in navigating the structure of the left ventricle, the fact that it requires arterial access and the potential problems associated with ablation of ventricular tissue, such as sudden cardiac death. The other approach is to introduce a transseptal sheath apparatus, a long single plane curve introducer, into the right femoral vein and advance it through the inferior vena cava into the right atrium. A puncture is then made through the fossa ovalis in the interatrial septum and the apparatus is advanced into the left atrium where the trocar and dilator of the apparatus are removed, leaving the sheath in position in the left atrium. The mapping or ablation catheter is then inserted through the sheath and into the left atrium and positioned on top of the mitral valve annulus near the anomalous conduction pathway. Specific positions may be chosen for the mapping or ablation on the left side of the heart, including specifically posterorseptal, posterior, posterorlateral, lateral and anterolateral positions around the mitral valve annulus.

Traditionally, there have been two techniques for locating and ablating anomalous conduction pathways which are situated between the right atrium and right ventricle. Either method can be initiated by advancing a catheter through an access site into a vein in the leg, neck or upper chest.

The first technique, which approaches the pathway from the pathway's ventricular insertion site, involves entering the right atrium from either the inferior or superior vena cava, passing through the tricuspid valve, and advancing toward the apex of the right ventricle. Then the catheter is directed to make a 180 degree turn to reverse its path back up toward the right atrium and locate the accessory pathway under the tricuspid valve apparatus. The accessory pathway is then ablated from the ventricular insertion site under the tricuspid valve.

The second technique, which approaches the pathway from the atrial insertion site, is to enter the right atrium from the inferior or superior vena cava, and attempt to locate the atrial insertion site of the accessory pathway around the tricuspid valve annulus. The accessory pathway is then ablated from the pathway's atrial insertion site on the atrial aspect of the tricuspid valve.

AV nodal pathways can be located and ablated from the right atrium.

Mere introduction of the catheter into the left atrium is not sufficient to effectively and efficiently perform these medical procedures, especially for the mapping or ablation of anomalous conduction pathways. These medical procedures are usually performed using a special catheter. The medical practitioners monitor the introduction of the catheter and its progress through the vascular system by a fluoroscope. Such fluoroscopes do not easily identify the specific features of the heart in general and the critically important structures of the right and left atrium in specific, thus making placement of the catheter difficult. This placement is especially difficult as the beating heart is in motion and the catheter will be moving within the right atrium and the left atrium as blood is being pumped through the heart throughout the procedure. The structure and shape of the guiding introducers of the instant invention addresses and solves these problems.

Referring now to FIGS. 3 through 6, the guiding introducer of the present invention for use in the left atrium is comprised of a first, second and third section. The first section is a conventional, generally elongated hollow, straight catheter section of sufficient length for introduction into the patient and for manipulation from the point of insertion to the specific desired location within the heart.

Merged with the distal end of the first section of the sheath is the second section which is curved in a compound curve, curving first upward and in a first longitudinal curve and simultaneously curving to the right in a second longitudinal curve. The first longitudinal curve has a radius of from about 0.5 cm. to about 2.0 cm. and preferably from about 0.5 cm. to about 1.5 cm. The arc of the first longitudinal curve is preferably from about 40 to about 60 degrees and most preferably from about 45 to about 55 degrees of arc. The second longitudinal curve of the second section contains a radius from about 0.5 cm. to about 4.0 cm., preferably from about 0.5 cm. to about 3.0 cm., and most preferably from about 0.5 to about 2.0 cm. The second longitudinal curve is preferably less than about 2.0 cm. in length.

The third section of the introducer is merged with the distal end of the second section. The structure of the third section of the guiding introducer will depend on its intended use. In one embodiment (FIGS. 3–5) the guiding introducer is used to place a mapping or ablating catheter in a position anterior to anterolateral to lateral to posterorlateral accessory pathways associated with the mitral valve annulus. To accomplish this, the third section is a third longitudinal curve wherein the plane of the third section is angled upward at an angle of approximately 40 to about 60 degrees, preferably 45 to about 55 degrees and, most preferably, 50 degrees from the plane of the first section and where substantially all of said third section is coplanar (at least within 15 degrees of coplanar).

To place sensing or ablating catheters at a specific location adjacent or left fibrous trigone, the arc of the third longitudinally curved section of the third section has a radius of about 35 to about 55 degrees, preferably from about 40 to about 50 degrees and, most preferably, about 45 degrees. See FIG. 3.

This guiding introducer can also be used for analysis and treatment of anterolateral to lateral accessory pathways of the mitral valve annulus. For this use the third longitudinally curved section of the third section is comprised of an arc with the radius of about 80 to about 100 degrees, preferably from about 85 to about 95 degrees and, most preferably, about 90 degrees. See FIG. 4.

The guiding introducer may also be used for analysis and treatment of lateral to posterolateral accessory pathways of the mitral valve annulus. In this embodiment the third longitudinally curved section is comprised of an arc with a radius of about 125 to about 145 degrees, preferably 130 to about 140 degrees and, most preferably about 135 degrees. See FIG. 5.

The guiding introducer may also be used for analysis and treatment of posterolateral to posteroseptal accessory pathways of the mitral valve. A somewhat different structure is present for this emodiment because of the structure of that portion of the left atrium of the heart. (See FIG. 6) While the first and second sections of this second preferred embodiment are the same as those of the first preferred embodiment, the angle of the plane of the third section in relationship to the plane of the first section is different. In this embodiment, the plane of the third section is angled upward at an angle from about 25 to about 45 degrees, preferably from about 30 to about 40 degrees, and most preferably about 35 degrees from the plane of the first section. In this embodiment the longitudinally curved section of the third section is comprised of an arc with a radius of about 170 to about 190 degrees, preferably 175 to about 185 degrees and, most preferably about 180 degrees.

The distal tip of the introducer may be, and preferably will be, tapered to form a good transition with the dilator as is the case with many introducers.

The guiding introducer may be made of any material suitable for use in humans and which has a memory or permits distortion from and subsequent substantial return to the desired three dimensional or complex multi-planar shape. For the purpose of illustration and not limitation, the internal diameter of the tip of the guiding introducer may vary from about 6 to about 10 "French" (1 French equals about ⅓ of a millimeter). Such introducer can accept dilators from about 6 to about 10 French and appropriate guidewires. Obviously, if larger or smaller dilators or catheters are used in conjunction with the guiding introducers of the instant invention, modifications in size or shape can be made to the instant guiding introducers.

The guiding introducer preferably may contain one or a multitude of radioopaque tip marker bands near the terminus of the guiding introducer. While various modifications may be made in the shapes by increasing or decreasing its size or adding additional tip markers, it is critical to the successful location of the guiding introducer within the atrium that the shape be maintained.

The guiding introducer also preferably contains one or a plurality of vents near the distal tip of the introducer, preferably three or four of such vents. The vents are preferably located no more than about 5.0 to 6.0 cm. from the tip of the introducer and more preferably 0.5 cm. to about 4.0 cm. from the tip. The size of these vents should be in the range of about 40 to 60 ¹⁄₁₀₀₀ of an inch in diameter. These vents are generally designed to prevent air embolisms from entering the introducer caused by the withdrawal of a catheter contained within the guiding introducer in the event the distal end of the introducer is ocluded. For example, if the tip of the introducer is placed against the myocardium and the catheter located within the introducer is withdrawn a vacuum may be created within the catheter if no vents are provided. If such vacuum is formed, air may be forced back into the introducer by the reintroduction of a catheter into the lumen of the introducer. Such air embolism could cause significant problems on the patient, including the possibility of a stroke, heart attack or other such problems common with air embolisms in the heart. The addition of vents near the distal tip of the guiding introducers prevents the formation of such vacuum by permitting fluid, presumably blood, to be drawn into the lumen of the introducer as a catheter is being removed from the introducer, thus preventing the possibility of the formation of an air embolism within the introducer.

Variances in size or shape of the instant guiding introducers are also intended to encompass pediatric uses for the guiding introducer of the instant invention although the preferred uses are for adult human hearts. It is well recognized that pediatric uses may require reductions in size of the various sections of the introducer, in particular the first section, but without any significant modification to the shape or curve of the guiding introducer.

In operation, a modified Seldinger technique is normally used for the insertion of the catheter into either an artery or vein of the body. Using this procedure, a small skin incision is made at the appropriate location to facilitate the catheter or dilator passage. The subcutaneous tissue is then dissected, followed by a puncture of the vessel with an appropriate needle with stylet positioned at a relatively shallow angle. The needle is then partially withdrawn and reinserted at a slightly different angle into the vessel, making sure that the needle remains within the vessel. A soft flexible tip of an appropriate sized guidewire is then inserted through and a short distance beyond the needle into the vessel. Firmly holding the guidewire in place, the needle is removed. The wire guide is then advanced through the vessel into the inferior vena cava or into the right atrium and finally the superior vena cava. With the wire guide in place, a dilator is then placed over the wire with the guiding introducer placed over the dilator. The dilator and guiding introducer generally form an assembly to be advanced together along the guidewire into the superior vena cava. After insertion of the assembly, the guidewire is then withdrawn. A Brockenbrough or trocar needle is then inserted through the lumen of the dilator to the right atrium to be used to create an opening through the interatrial septum, preferably at the fossa ovalis. The entire assembly (dilator sheath and Brockenbrough needle) is withdrawn from the superior vena cava into the right atrium so the tip rests against the intraatrial septum at the level of the fossa ovalis. The Brockenbrough needle is then advanced within the dilator to reach the fossa ovalis. After the opening is made through the interatrial septum, the needle, dilator and guiding introducer are advanced into the left atrium. After the guiding introducer of the instant invention is advanced through the interatrial septum into the left atrium, the Brockenbrough or trocar and dilator are removed, leaving the guiding introducer in the left atrium. The catheter to be used for analysis and/or treatment of the anomalous conduction pathways is then advanced through the lumen of the guiding introducer and is placed at an appropriate location near the mitral valve annulus. The choice of the guiding introducer to be used will depend on the location of the anomalous conduction pathway, as has previously been discussed.

By choice of the desired predetermined shape of the guiding introducer in conjunction with fluoroscopic viewing, the distal portion of the guiding introducer can be manipulated to direct the distal end of a catheter placed within the lumen of the guiding introducer, to a specific internal surface with the left atrium. In addition, by providing sufficient rigidity and support as the introducer is held in place by the anatomical structure of the heart as well as the vasculature, the distal end of the guiding introducer can be maintained in that fixed location or surface position of the endocardial structure to permit the appropriate procedures to be performed. If sensing procedures are involved, the guiding introducer is placed in the desired location. At that point, the electrical activity of the heart peculiar to that location can be precisely determined by use of a sensing electrophysiology catheter placed within the guiding introducer. Further, as the guiding introducer permits precise location of catheters, an ablation catheter may be placed at a precise location for destruction by the use of energy, for example, radiofrequency, thermal, laser or direct current. This precise location of the ablation catheter tip is important as there will be no dilution of the energy delivered due to unfocused energy being dissipated over the entire cardiac chamber and lost in the circulating blood by a constantly moving tip of the ablating catheter. This permits a significantly reduced amount of energy to be applied while still achieving efficient ablation. Further, time used to perform the procedure is significantly reduced over procedures where no guiding introducer is used.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A method for mapping and ablation of anomalous conduction pathways associated with a left atrium of a heart comprising the steps of:

(a) introducing into the left atrium of the heart a precurved, guiding introducer, wherein said introducer contains a lumen passing therethrough, a proximal end and a distal end;

(b) introducing into the lumen of the precurved, guiding introducer a catheter for mapping and ablation of anomalous conduction pathways within the left side of the heart, wherein said catheter has one or more electrodes located at or near a distal tip of the catheter; and (c) extending said distal tip of the catheter through the lumen of the guiding introducer and beyond the distal tip of the guiding introducer to allow the electrodes of the catheter to map and ablate one or more anomalous conduction pathways within the left side of the heart.

2. The method for mapping and ablation of anomalous conduction pathways of claim 1 including ablating anomalous conduction pathways utilizing an energy source chosen from radio frequency, thermal, laser or direct current.

3. The method for mapping and ablation of anomalous conduction pathways of claim 2 including ablating utilizing radio frequency energy.

4. The method for mapping and ablation of anomalous conduction pathways of claim 1 including utilizing a guiding introducer comprised of a first, second and third section, wherein the first section is a generally elongated straight section, wherein merged with a distal end of said first section is the second section, wherein the second section is curved, in a compound curve, curving first in a first curve and next curving in a second curve, wherein the second section merges with the third section, wherein the third section is comprised of a third curve.

5. The method for mapping and ablation of anomalous conduction pathways of claim 1 including utilizing a guiding introducer comprised of a first, second and third sections, wherein the first section is a generally elongated straight section, wherein merged with a distal end of said first section of said introducer is the second section which is a curved section wherein said curved section is curved in a compound curve curving in a first curve with a radius of about 0.5 cm. to about 2.0 cm. to form an arc of approximately 40 degrees to 60 degrees, and simultaneously curving in a second curve containing a radius of from about 0.5 cm. to about 4.0 cm., wherein said second section is less than about 2.0 cm. in overall length, wherein merged with the distal end of the second section is the third section comprised of a third curve with a radius of from about 1.5 cm. to about 4.0 cm., wherein said third section is directed at an angle of approximately 40 degrees to about 60 degrees from the first section and wherein substantially all of said third section is coplanar.

6. The method for mapping and ablation of anomalous conduction pathways of claim 5 wherein the third curve has an arc of about 35–55 degrees.

7. The method for the mapping and ablation of anomalous conduction pathways of claim 5 wherein the third curve has an arc of about 80–100 degrees.

8. The method for the mapping and ablation of anomalous conduction pathways of claim 5 wherein the third curve has an arc of about 125–145 degrees.

9. The method for mapping and ablation of anomalous conduction pathways of claim 1 including utilizing a guiding introducer in a left atrium of the human heart is comprised of a first, second and third section, wherein the first section is a generally elongated straight section, wherein merged with a distal end of said first section is the second section, wherein the second section is curved in a compound curve first curving in a first curve and then curving in a second curve, wherein the distal end of the second section merges with the third section which is a third curve, wherein said third section is angled in an angle of about 25 degrees to about 45 degrees from the first section and wherein substantially all of said third section is coplanar.

10. The method for mapping and ablation of anomalous conduction pathways of claim 1 wherein the guiding introducer to be used in the left atrium of the human heart is comprised of a first, second and third sections wherein, the first section is a generally elongated straight section, wherein merged with distal end of said first section is the second section, wherein the second section is curved in a compound curve first curving in a first curve with a radius of from about 0.5 cm. to about 2.0 cm. for about 40 degrees to about 60 degrees of arc and then curving in a second curve containing a radius of about 0.5 to about 4.0 cm., wherein said second section is less than about 2.0 cm. in overall length, wherein the distal end of the second section merges with the third section, which is a third curve with a radius of from about 1.5 cm. to about 4.0 cm., wherein the third section is angled at an angle of about 25 degrees to about 45 degrees from the first section, and wherein substantially all of said third section is coplanar.

11. The method for mapping and ablation of claim 10 wherein the third curve has an arc of about 170–190 degrees.

12. A method for treatment of Wolfe-Parkinson-White syndrome associated with a left atrium of a heart comprising the steps of:

(a) introducing into the left atrium of the heart a precurved, guiding introducer, wherein said introducer contains a lumen passing therethrough, a proximal end and a distal tip;

(b) introducing into the lumen of the precurved, guiding introducer a catheter within the left atrium of the heart wherein said catheter has one or more electrodes located at or near a distal tip of the catheter;

(c) extending said distal tip of the catheter through the lumen of the introducer and beyond the distal tip of the introducer to permit the electrodes of the catheter to ablate anomalous conduction pathways within the left atrium of the heart as a treatment for Wolfe-Parkinson-White syndrome.

13. The method for treatment of Wolfe-Parkinson-White syndrome of claim 12 including utilizing the guiding introducer comprised of a first, second and third sections, wherein the first section is a generally elongated straight section, wherein merged with a distal end of said first section of said introducer is the second section which is a curved section wherein said curved section is curved in a compound curve curving from the first section in a first curve with a radius of about 0.5 cm. to about 2.0 cm. to form an arc of approximately 40 to about 60 degrees, and curving in a second curve containing a radius of from about 0.5 cm. to about 4.0 cm., wherein said second section is less than about 2.0 cm. in length, wherein merged with the distal end of the second section is the third section, comprised of a third curve with a radius of from about 1.5 cm. to about 4.0 cm., wherein said third section is directed at an angle of approximately 40 degrees to about 60 degrees from the first section and wherein substantially all of said third section is coplanar.

* * * * *